United States Patent
Troner

(10) Patent No.: US 9,439,988 B2
(45) Date of Patent: Sep. 13, 2016

(54) ELECTRIC HAND SANITIZER

(71) Applicant: Adam Troner, San Mateo, CA (US)

(72) Inventor: Adam Troner, San Mateo, CA (US)

( * ) Notice: Subject to any disclaimer, the term of this patent is extended or adjusted under 35 U.S.C. 154(b) by 0 days.

(21) Appl. No.: 13/958,585

(22) Filed: Aug. 4, 2013

(65) Prior Publication Data

US 2015/0037020 A1  Feb. 5, 2015

(51) Int. Cl.
*H05B 3/40* (2006.01)
*A61L 2/06* (2006.01)
*A61L 2/00* (2006.01)

(52) U.S. Cl.
CPC .............. *A61L 2/06* (2013.01); *A61L 2/0023* (2013.01); *A61L 2202/14* (2013.01)

(58) Field of Classification Search
CPC ............. H05B 3/82; H05B 3/48; H05B 3/80
USPC .......... 134/102.2–102.3, 174, 182, 199, 113, 134/200–201; 392/384–385, 379, 380–383, 392/497
See application file for complete search history.

(56) References Cited

U.S. PATENT DOCUMENTS

| 2,814,081 | A | | 11/1957 | Stevenson | |
| 5,074,322 | A | * | 12/1991 | Jaw | 134/56 R |
| 5,498,394 | A | | 3/1996 | Matschke | |
| 5,727,579 | A | * | 3/1998 | Chardack | 134/95.2 |
| 6,431,189 | B1 | * | 8/2002 | Deibert | 134/57 R |
| 8,142,713 | B2 | | 3/2012 | Gordon | |
| 8,155,508 | B2 | | 4/2012 | Caine | |
| 2008/0052952 | A1 | | 3/2008 | Nelson | |

FOREIGN PATENT DOCUMENTS

EP  WO2012076521 A1  6/2012

\* cited by examiner

*Primary Examiner* — Phuong Nguyen

(57) ABSTRACT

A device for sanitizing human hands. One embodiment, comprising of a casing shell containing a heating element, an air displacement means, and a cavity that is able to accommodate a human hand.

1 Claim, 3 Drawing Sheets

ELECTRIC HAND SANITIZER

CROSS-REFERENCE TO RELATED APPLICATIONS

This application claims the benefit of provisional patent application Ser. No. 61/742,294, filed Aug. 7, 2012 by the present inventor.

BACKGROUND

Prior Art

The following is a tabulation of some prior art that presently appears relevant:

| U.S. Patents | | | |
|---|---|---|---|
| Pat. No. | Kind Code | Issue Date | Patentee |
| 2,814,081 | B1 | 1957-11-26 | Stevenson |

| U.S. Patent Application Publications | | | |
|---|---|---|---|
| Publication Nr. | Kind Code | Publ. Date | Applicant |
| U.S. Pat. No. 5,498,394 | A | 1996-03-12 | Matschke |
| U.S. Pat. No. 8,142,713 | B2 | 2012-03-27 | Gordon |

| Foreign Patent Documents | | | |
|---|---|---|---|
| Foreign Doc. Nr. | Cntry Code | Kind Code Pub. Dt | App or Patentee |
| WO2012076521 | EP | A1  2012-06-14 | Graydon |

People are concerned about reducing the bacteria present on their hands. The current methods used to reduce the presence of bacteria on hands include using an alcohol based hand gel or using a UV (Ultraviolet) light/radiation. There are other devices designed to dry hands that are used in public restrooms.

Recent media articles report the worry that the overuse of antibacterial gels and soaps may be contributing to the creation of drug-resistant mutant germs.

People need a solution that does not rely on hand gel and is economical.

All the hand sanitizer devices heretofore known suffer from a number of disadvantages:
   (a) The use of UV light/radiation is costly.
   (b) The reliance on some form of alcohol based gel or spray.
   (c) The use of antibacterial soap or gel.

Advantages

Although others have invented alcohol based hand gels, UV (Ultraviolet) sanitizers, and public bathroom hand dryers, various aspects of my electric hand sanitizer may have one or more of the following advantages:
   does not require an alcohol based gel
   does not require a UV light/radiation
   provides a more accessible option for hands
   is easily placed in a wide range of locations
   blows hot air into a cavity
   is less awkward to use.

DRAWINGS —FIGURES

DETAILED DESCRIPTION —FIG. 2—FIRST EMBODIMENT

Figure 1:
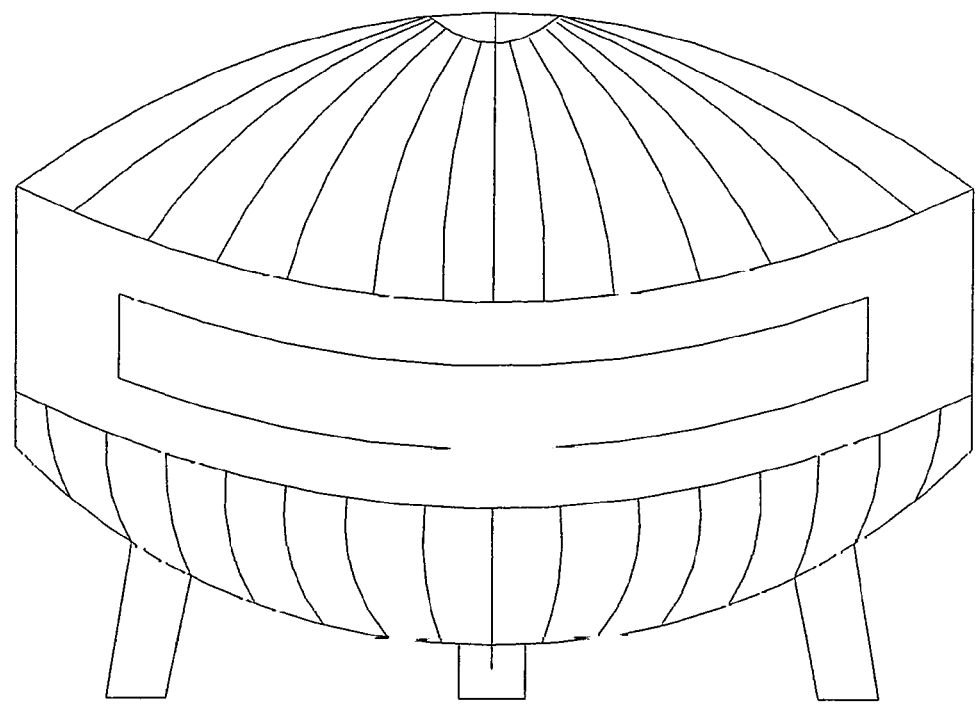
FIG. 1 shows a perspective view from above in accordance with one embodiment.
Figure 2:
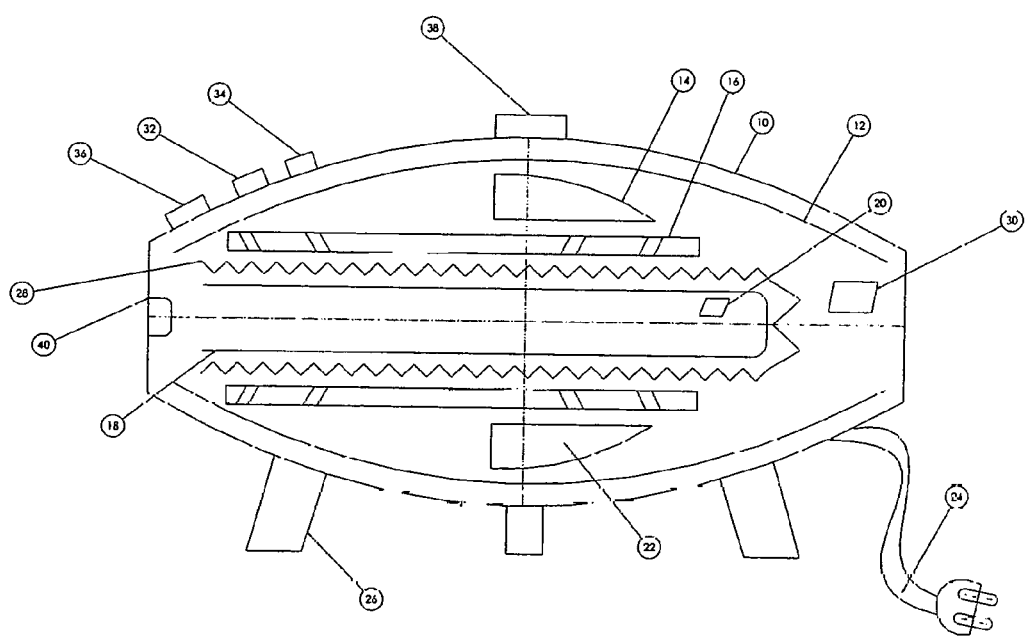
FIG. 2 shows an internal/side view cut away in accordance with one embodiment.
Figure 3:
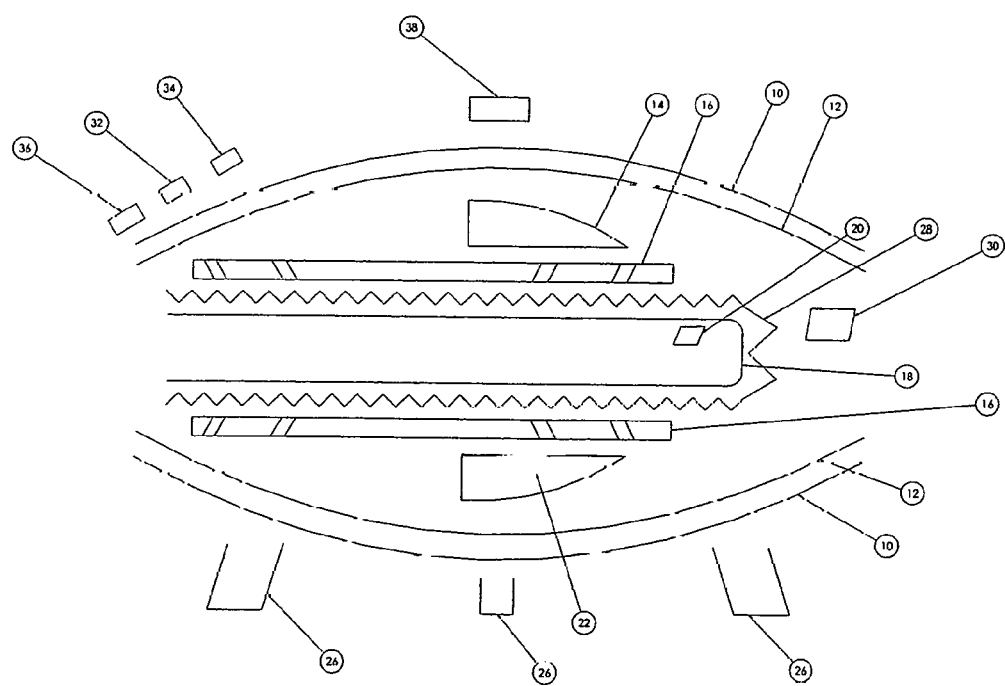
FIG. 3 shows an exploded view in accordance with one embodiment.

The components of my invention are:
   a casing shell
   insulation
   a heating element
   an array of fans
   a motion sensor
   a power supply
   an electrical plug/power cord
   a logic chip
   a power light
   an in-use light
   a power button
   a stop button
   a protective lining
   footings One embodiment of the device is shown in FIG. 2. The device has an electrical plug cord 24 connected to a power supply 22 which is affixed to the bottom portion of a casing 10. The casing 10 is stabilized by footings legs 26. An internal frame 28 is mounted within the casing 10. Secured to the internal frame 28 is a motion sensor 20 and logic chip 30. A heating element 14 is attached to the top of the casing 10. The heating element is connected to an array of fans 16. A protective lining 18 lines the interior of the internal frame 28, forming a cavity 40. Insulation 12 lines the casing 10 around the heating element 14. A power light 32, an in-use light 34, a power button 36, and a stop button 38 are all attached to the top of the casing 10.

The method or arrangement of wiring or connecting the above electronic components and mounting them in a case will be well known to those with ordinary skill in the electronic and mechanical arts.

Operation—FIG. 2

My electric hand sanitizer achieves its result as follows: A user of the electric hand sanitizer places the desired hand into the cavity 40. The motion sensor 20 is activated and the in-use light 34 turns on. Power from the power supply 22 is sent to the heating element 14 which generates heat. That heat is evenly dispersed throughout the cavity 40 using the array of fans 16. The user waits the number of seconds until the fans 16 stop blowing and the in-use light 34 turns off. The user then withdraws their hand. The user would then repeat the process for their other hand if desired.

Alternative Embodiments

There are many alternative ways that my electric hand sanitizer can be implemented:
   A different power source can be used, for example—a battery, USB, or car socket.
   The casing can be different shapes, for example—the shape of a hand.
   The casing can be different colors.
   A different electrical plug connector (i.e. shock protection) can be used.
   There could be different sizes of the device for a range of hand sizes.
   The orientation of the device could be modified (i.e. standing up or laying flat).
   A manual push button could be used to activate the device.

It could be sized for use with a human foot.
The amount of time the fans blow could be modified.
The temperature of the hot air being blown could be modified.
More or fewer fans could be used.
Fans could be placed outside the casing.
A cooling fan (i.e. no heat) could be added to follow the use of the heat fan.
A quiet version of a fan could be used.
Exhaust fans could be attached.
A light could turn on when the process is complete.
A sound could chime when the process is complete.
The cavity opening can be different shapes, for example—elliptical, or rectangular.
There could be two cavities allowing both hands to use the device simultaneously.
It could connected to a computer network or the cloud.

CONCLUSION, RAMIFICATIONS, AND SCOPE

Accordingly, the reader will see that at least one embodiment of the electric hand sanitizer provides a more easily maintainable yet economical device that can be used by persons of any age for hand sanitization.

Although the description above contains many specificities, these should not be construed as limitations on the scope, but rather as an exemplification of one [or several] embodiment(s) thereof. Many other variations are possible. For example, the casing can have other shapes, such as in the form of a hand, etc.; the casing can have other sizes; the casing can have other colors; the cavity opening can have other shapes, such as elliptical, rectangular, round, etc; the cavity can have other sizes; the power supply can have other sources, such as a battery, USB, car socket, etc.

Thus the scope of the embodiments should be determined by the appended claims and their legal equivalents, rather than by the examples given.

I claim:

1. An electric hand sanitizing device, comprising:
   a casing shell with an internal cavity that is able to accommodate a human hand,
   a heating element in said casing shell for generating heat,
   an array of fans in said casing shell for directing the heat from said heating element into said internal cavity,
   a power light for indicating said device is connected to a power supply,
   an in-use light for indicating said device is being operated,
   a motion sensor for detecting movement of said human hand,
   a logic chip for driving the process of said device,
   an internal frame in said casing shell for securing said motion sensor and said logic chip,
   a protective lining in said internal frame for protecting said human hand,
   a lining of insulation in said casing shell for reducing the heat transfer from said heating element, and
   a power button configured to control dispensing heat from said heating element and said array of fans to said human hand when said human hand is placed in said internal cavity, whereby said human hand is being reduced of bacteria present,
   wherein said electric hand sanitizing device does not require an alcohol based gel and a UV light/radiation.

* * * * *